United States Patent
Elyahoodayan et al.

(10) Patent No.: US 12,263,342 B2
(45) Date of Patent: Apr. 1, 2025

(54) SENSORS AND METHODS FOR DETERMINING RESPIRATION

(71) Applicant: The Alfred E. Mann Foundation for Scientific Research, Valencia, CA (US)

(72) Inventors: Sahar Elyahoodayan, Los Angeles, CA (US); Brian M. Shelton, Altadena, CA (US); Neil H. Talbot, La Crescenta, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 518 days.

(21) Appl. No.: 17/519,211

(22) Filed: Nov. 4, 2021

(65) Prior Publication Data

US 2022/0134103 A1    May 5, 2022

Related U.S. Application Data

(60) Provisional application No. 63/109,491, filed on Nov. 4, 2020.

(51) Int. Cl.
  *A61N 1/36*    (2006.01)
(52) U.S. Cl.
  CPC ........ *A61N 1/3611* (2013.01); *A61N 1/36135* (2013.01); *A61N 1/36139* (2013.01)
(58) Field of Classification Search
  CPC .............. A61N 1/3611; A61N 1/36135; A61N 1/36139
  USPC ..................................................... 607/2, 42
  See application file for complete search history.

(56) References Cited

U.S. PATENT DOCUMENTS

| | | |
|---|---|---|
| 5,540,731 A | 7/1996 | Testerman |
| 8,938,299 B2 | 1/2015 | Christopherson et al. |
| 2005/0115561 A1* | 6/2005 | Stahmann .............. A61B 5/103 128/204.23 |
| 2008/0285805 A1 | 11/2008 | Luinge et al. |
| 2012/0065524 A1* | 3/2012 | Morren ................ A61B 5/1102 73/514.01 |

(Continued)

FOREIGN PATENT DOCUMENTS

EP    2008581 A2    12/2008

OTHER PUBLICATIONS

International Search Report, issued by International Searching Authority in corresponding International Application No. PCT/US2021/072248, mailed Feb. 28, 2022.

(Continued)

*Primary Examiner* — Ankit D Tejani
(74) *Attorney, Agent, or Firm* — ARENTFOX SCHIFF LLP

(57) ABSTRACT

The disclosure provides systems and methods for treating obstructive sleep apnea using an inertial measurement unit (IMU) comprising an accelerometer and a gyroscope, wherein the IMU is configured to detect chest and/or abdominal movement by a patient during the inspiration and expiration stages of a respiratory cycle and to generate positional data based on the detected movement. Positional data generated by the IMU is used by an implanted stimulation system to determine when to deliver electrical stimulation to a nerve which innervates an upper airway muscle, such as the hypoglossal nerve, to treat sleep apnea.

27 Claims, 5 Drawing Sheets

(56) References Cited

U.S. PATENT DOCUMENTS

| | | | | |
|---|---|---|---|---|
| 2014/0228905 | A1* | 8/2014 | Bolea | A61F 5/566 |
| | | | | 607/42 |
| 2015/0164375 | A1* | 6/2015 | Schindhelm | A61B 5/103 |
| | | | | 600/534 |
| 2018/0000450 | A1* | 1/2018 | Tsuyuki | A61B 8/543 |
| 2019/0133537 | A1* | 5/2019 | Ghose | A61B 5/7278 |
| 2019/0223782 | A1* | 7/2019 | Wen | A61B 5/4818 |
| 2020/0100727 | A1* | 4/2020 | Colas | A61B 5/725 |
| 2020/0129126 | A1 | 4/2020 | Kovoor et al. | |
| 2020/0170527 | A1* | 6/2020 | Kale | A61B 5/7267 |
| 2023/0263431 | A1* | 8/2023 | Gadrey | A61B 5/7275 |
| | | | | 600/534 |

OTHER PUBLICATIONS

International Search Report and Written Opinion, issued by International Searching Authority in corresponding International Application No. PCT/US2021/072247, mailed Mar. 7, 2022.

* cited by examiner

SENSORS AND METHODS FOR DETERMINING RESPIRATION

CROSS-REFERENCE TO RELATED APPLICATION

This application claims the benefit of U.S. Provisional Application Ser. No. 63/109,491, entitled "SYSTEMS AND METHODS FOR RESPIRATION DETECTION," which was filed on Nov. 4, 2020, and is expressly incorporated by reference herein in its entirety.

BACKGROUND

Obstructive Sleep Apnea (OSA) is a sleep disorder involving obstruction of the upper airway during sleep. The obstruction of the upper airway may be caused by the collapse of or increase in the resistance of the pharyngeal airway, often resulting from tongue obstruction. The obstruction of the upper airway may be caused by reduced genioglossus muscle activity during the deeper states of NREM sleep. Obstruction of the upper airway may cause breathing to pause during sleep. Cessation of breathing may cause a decrease in the blood oxygen saturation level, which may eventually be corrected when the person wakes up and resumes breathing. The long-term effects of OSA include high blood pressure, heart failure, strokes, diabetes, headaches, and general daytime sleepiness and memory loss, among other symptoms.

OSA is extremely common, and may have a prevalence similar to diabetes or asthma. Over 100 million people worldwide suffer from OSA, with about 25% of those people being treated. Continuous Positive Airway Pressure (CPAP) is a conventional therapy for people who suffer from OSA. More than five million patients own a CPAP machine in North America, but many do not comply with use of these machines because they cover the mouth and nose and, hence, are cumbersome and uncomfortable.

Neurostimulators may be used to open the upper airway as a treatment for alleviating apneic events. Such therapy may involve stimulating the nerve fascicles of the hypoglossal nerve (HGN) that innervate the intrinsic and extrinsic muscles of the tongue in a manner that prevents retraction of the tongue which would otherwise close the upper airway during the inspiration period of the respiratory cycle. ImThera Medical is currently in FDA clinical trials for a stimulator system that is used to stimulate the trunk of the HGN with a nerve cuff electrode. The stimulation system does not provide a sensor or sensing, and therefore, the stimulation delivered to the HGN trunk is not synchronized to the respiratory cycle. Thus, the tongue and other muscles that are innervated by nerve fascicles of the HGN trunk are stimulated irrespective of the respiratory cycle.

The rationale for this treatment method appears to be that it is enough simply to tone the tongue muscle and other nearby muscles, so that the tongue muscle does not retract in a manner that would cause OSA. The belief is that it is not necessary to specifically target the protraction (i.e., anterior movement) of the tongue muscle and to synchronize the occurrence of tongue protraction when it is most needed, i.e., during inspiration. The nerve cuff electrode of the ImThera Medical system has multiple electrode contacts helically surrounding the proximal part of the HGN nerve trunk. So, instead, each electrode contact delivers stimulation in a sequential order to the HGN trunk. For example, if a three-electrode contact nerve cuff is used, electrode contact #1 stimulates, then stops, electrode contact #2 stimulates, then stops, electrode contact #3 stimulates, then stops, then electrode contact #1 stimulates, then stops and so on. Since all or most electrode contacts deliver stimulation, there is no selection process to choose the best one or two electrode contacts that is finally used to deliver the best stimulation to alleviate sleep apnea.

A disadvantage of the ImThera Medical system is that it does not target tongue protraction coincident with the inspiration phase of respiration, since it does not have a sensor to enable synchronized stimulation of the respiratory cycle. Since there is no attempt to synchronize the stimulation with the respiratory cycle, the tongue protraction does not occur when it would appear to help the most—during inspiration when OSA can occur. Also, because the HGN trunk contains nerve fascicles that innervate muscles other than the muscle that extend the tongue, the Imthera Medical method of stimulation at the HGN trunk does not just target the specific protrusor muscles of the tongue muscle, but other muscles that are not targeted. Thus, stimulating the HGN trunk in an arbitrary manner may recruit other nerve fascicles of the HGN trunk that may not contribute to the protraction of the tongue.

Another company, Inspire Medical Systems, Inc., does offer a stimulation system with a sensor, and therefore does attempt to time the onset of stimulation to the breathing cycle. This system, which is FDA approved for sale in the United States since April 2010, uses a simple, tripolar electrode (one working and two return electrode contacts only) within a nerve cuff electrode and implants the electrode at the branch of the HGN that is responsible for protruding the tongue. A simple, two-electrode contact or three-electrode contact cuff electrode can be used at the branch nerve, unlike the HGN trunk, because at the distal branch location, the nerve fascicles generally innervate the specific tongue protrusor muscle and not other muscles.

However, implanting the electrode at a branch of the HGN requires additional surgery time, which increases trauma to the patient and increases the substantial expense of operating room time. By attaching the nerve cuff electrode to the proximal section of the main trunk of the HGN, compared to placing the nerve cuff electrode at the more distal end of the HGN, the surgical time may be reduced by approximately one hour or more. Further, because the branch nerve is small and more difficult to isolate than the HGN trunk, implanting a nerve cuff electrode at the branch site demands heightened expertise from the otolaryngologist/Ear Nose and Throat (ENT) surgeon or neurosurgeon, which may increase the chance for error and surgical risks. Furthermore, because the distal location of the HGN has a smaller diameter of nerves, and hence the required electrodes need to be smaller, the smaller nerve cuff electrode may be more difficult to manufacture.

Thus, it is certainly desirable to implant the nerve cuff electrode at the trunk of the hypoglossal nerve. However, one must then deal with the fact that the target nerve fascicles may be near the center of the nerve trunk and are not easily isolated and stimulated, while at the same time avoiding stimulating other non-targeted fascicles in the same nerve trunk.

A pressure sensor is connected to neurostimulator of the Inspire system by a lead, thereby allowing the pressure sensor to be placed remotely from the implanted site of the neurostimulator. However, the fact that the pressure sensor has a lead connected to the stimulator necessitates some additional surgery, because the sensor lead is another appendage that must be implanted.

As illustrated by the foregoing summary, current systems for treating OSA either use pressure sensors near the diaphragm to detect the start of inspiration or use no inspiration detection at all. Furthermore, the use of a pressure sensor that is distal to an implantable pulse generator (IPG) requires a longer surgery. Thus, there remains a need for improved systems and methods for selectively recruiting only the fascicles of the hypoglossal nerve in synchronization with the respiratory cycle for treating OSA of a patient, while minimizing the surgery time and effort required to implant the neurostimulation components in the patient. There exists further needs for systems and methods which can provide increased accuracy with respect to the detection of a subject's respiratory cycle and leverage this increased accuracy to better treat subjects suffering from OSA.

BRIEF SUMMARY OF EXEMPLARY ASPECTS OF THE DISCLOSURE

Ideally, an OSA stimulator should begin stimulation immediately before the start of inspiration, continue stimulation throughout inspiration, and stop stimulation at the end of the inspiration. Continual stimulation can result in therapeutic fatigue, decreased efficacy, and a shorter recharge interval. The present disclosure addresses these and other shortcomings by providing systems and methods that can accurately detect inspiration and/or expiration, as well as the orientation of a patient (e.g., a human subject), using an inertial measurement unit (IMU) configured to generate chest positional data based on a patient's orientation. In some aspects, positional data from the IMU is paired with respiratory data from a microphone (or other acoustic sensor) and/or an electrocardiogram (ECG) sensor, to further improve accuracy or to provide additional functionality.

The IMU can reside within the housing of an IPG or in a separate housing (e.g., implanted in proximity to the IPG). The IMU is designed to detect chest and/or abdominal movement and orientation data for a patient, which is in turn processed by a controller coupled to both the IMU and the stimulation system, in order to accurately determine the starting and end points of a subject's inspiration cycle, allowing for precise administration of stimulation. The IMU-based systems described herein are particularly advantageous with respect to reducing surgical and recovery times because they can be integrated into the IPG or implanted in proximity to it. Earlier systems have used pressure sensors implanted in-between a patient's ribs to detect movement of the patient's thoracic or abdominal cavity during respiration. However, these earlier systems require significant surgical time and tunneling a lead to this space is invasive, resulting in a longer recovery time.

The following presents a simplified summary of several exemplary embodiments in order to provide a basic understanding of the inventions described herein. This summary is not intended as an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

In a first general aspect, the disclosure provides a system for treating obstructive sleep apnea in a patient that includes an IMU comprising an accelerometer and a gyroscope, wherein the IMU is configured to detect chest and/or abdominal movement by a patient (e.g., a human subject) during the inspiration and expiration stages of a respiratory cycle, and to generate positional data based on the detected movement; and a stimulator comprising (a) a stimulation system configured to deliver stimulation to a nerve which innervates an upper airway muscle; and (b) a controller coupled to the stimulation system, and to the IMU, wherein the controller is configured to trigger the stimulation system to stimulate the nerve based on the positional data generated by the IMU. As used herein, the term "respiratory cycle" refers to the timing of inspiration and expiration and respiratory rate of a patient.

In some aspects, the accelerometer comprises a 3-axis accelerometer and/or the gyroscope comprises a 3-axis gyroscope. In some aspects, the positional data comprises movement of the patient's chest and/or abdomen over time.

In some aspects, the system includes additional sensors other than the IMU. For example, the system may further comprise a microphone and/or an ECG sensor coupled to the controller. These optional additional sensors may be used to supplement the functionality of the system. For example, the controller may be configured to determine an apnea-hypopnea index (AHI) based on: (a) body positional data (e.g., chest and/or abdominal positional data); and (b) an audio signal detected by a microphone or a heart rate signal detected by an ECG sensor. In some aspects, the controller may be further be configured to trigger the stimulation system to stimulate the nerve based on an audio signal detected by a microphone, or based on a heart rate signal detected by an ECG sensor.

In some aspects, the chest positional data generated by the IMU and/or sensor data generated by the optional additional sensors, is processed by the controller, e.g., to determine a signal-to-noise (SNR) ratio or to filter the data. In some aspects, the system is configured to filter movement data detected by the IMU using at least one low-pass filter (LPF), high-pass filter (HPF), or band-pass filter (BPF). For example, the system may be configured to filter movement data detected by the IMU using a filter that has an upper cut-off frequency of 0.45 to 2 Hz, or a high-pass cut-off frequency of 0.05 to 0.1 Hz.

In some aspects the system may comprise: a) at least one hardware-based LPF or HPF; and/or b) at least one digital LPF or HPF. The at least one digital LPF or HPF may comprise software executed, e.g., by the controller. The LPFs and/or HPFs may be configured to have a variety of different cut-off frequencies. For example, in some aspects the at least one LPF is configured to have a frequency cut-off of 0.45 Hz to 2 Hz or lower for the IMU. In some aspects, the at least one LPF is configured to have a frequency cut-off of 500 Hz to 1.5 kHz or lower for the acoustic sensor. In some aspects, the at least one HPF is configured to have a frequency cut-off of 0.05 Hz to 0.1 Hz for the IMU and 50 Hz to 150 Hz for the acoustic sensor. In some aspects, the system comprises at least one BPF configured to have high and low frequency cut-offs which match any of the frequency cut-offs used by the LPFs or HPFs described herein.

In some aspects, the controller may be configured to operate in multiple modes. For example, the controller may be configured to determine an SNR of the movement and/or positional data detected or generated by the IMU, and to operate in an asynchronous mode when the SNR falls below a predetermined threshold (e.g., when the quality of the signal does not allow precise detection of inspiration and expiration). In this asynchronous mode, the controller may be configured to cause the stimulation system to stimulate the nerve based on a specific schedule or using other criteria that do not rely upon access to accurate positional data. For example, the controller may be configured to cause the stimulation system to stimulate the nerve throughout inspiration and expiration, for every other respiratory cycle of the patient. In some aspects, the SNR may be determined using historical positional data for the patient stored in a log. Such historical data may, e.g., be from the last 1 to 5 minutes of the respiratory data when the SNR was above a preset threshold.

In some aspects, the asynchronous mode is a mode wherein the controller is configured to cause the stimulation system to stimulate the nerve: a) for at least, exactly, or approximately 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 seconds; b) for X-Y seconds, where "X" and "Y" are each independently selected from 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15; c) for at least one full respiration cycle, wherein the start of the respiratory cycle is predicted based on previously logged respiratory rate data, and then optionally to cease stimulation for an equal amount of time; or d) for at least one full respiration cycle, wherein the start of the respiratory cycle is predicted based on previously logged respiratory rate data, and then optionally to cease stimulation for at least, exactly, or approximately 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 seconds.

In some aspects, the controller is configured to determine a respiratory cycle of the patient by: a) filtering chest and/or abdominal movement data detected by the IMU; and b) performing a principal component analysis (PCA) on the filtered chest and/or abdominal movement data. In some aspects, the PCA comprises: a) receiving a signal comprising 3D chest and/or abdominal movement data from the accelerometer component of the IMU, wherein the accelerometer comprises a 3-axis accelerometer and/or a 3D gyroscope; b) processing the signal using at least one filter; c) generating a covariance matrix based on the processed signal; d) computing eigenvectors and eigenvalues for the covariance matrix; and e) constructing a projection matrix that transforms the 3D chest and/or abdominal movement data into a single dimension.

In some aspects, the IMU comprises a 3-axis accelerometer and/or a 3-axis gyroscope, and the SNR is determined based upon a) at least two out of the three axes of the accelerometer; and/or b) at least two out of the three axes of the gyroscope. In some aspects, the accelerometer is a 3-axis accelerometer and the controller is configured to determine whether the SNR of at least two out of the three axes of the accelerometer are above a predetermined threshold and to use the strongest component signal to determine the respiratory cycle of the patient. In some aspects, the gyroscope is a 3-axis gyroscope and the controller is configured to determine whether the SNR of at least two out of the three axes of the gyroscope are above a predetermined threshold and to use the strongest component signal to determine the respiratory cycle of the patient.

In some aspects, the accelerometer is a 3-axis accelerometer and the controller is configured to determine a body orientation of the patient using the 3 axes of the accelerometer. For example, the controller may be configured to determine whether a patient is lying prone, supine, or lateral based on gravitational vectors (optionally accounting for the amount of time spent in a given orientation).

In a second general aspect, the disclosure provides methods of treating sleep apnea using any one of the systems described herein. For example, in some aspects the disclosure provides a device for use in treating sleep apnea, comprising any of the systems described herein. It is understood that a method of treating sleep apnea may comprise any combination of the steps or parameters described herein. For example, a method of treating obstructive sleep apnea in a patient may comprise: detecting chest and/or abdominal movement by the patient during the inspiration and expiration stages of a respiratory cycle using an inertial measurement unit (IMU) comprising an accelerometer and a gyroscope; generating, by the IMU, positional data based upon the detected movement, wherein positional data comprises information describing movement of the chest and/or abdomen of the patient, and optionally the patient's orientation; determining, by a controller coupled to the IMU, a respiratory waveform corresponding to a respiratory cycle of the patient, using the positional data; and stimulating a nerve innervating an upper airway muscle of the patient based on the respiratory waveform.

In some aspects, the methods described herein may further comprise a step of acquiring a sensory data from optional additional sensors (e.g., an acoustic sensor such as a microphone, or an ECG sensor); and apneic events may be determined based on the extracted respiratory waveform and the second set of sensory data.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

DETAILED DESCRIPTION

Figure 1:
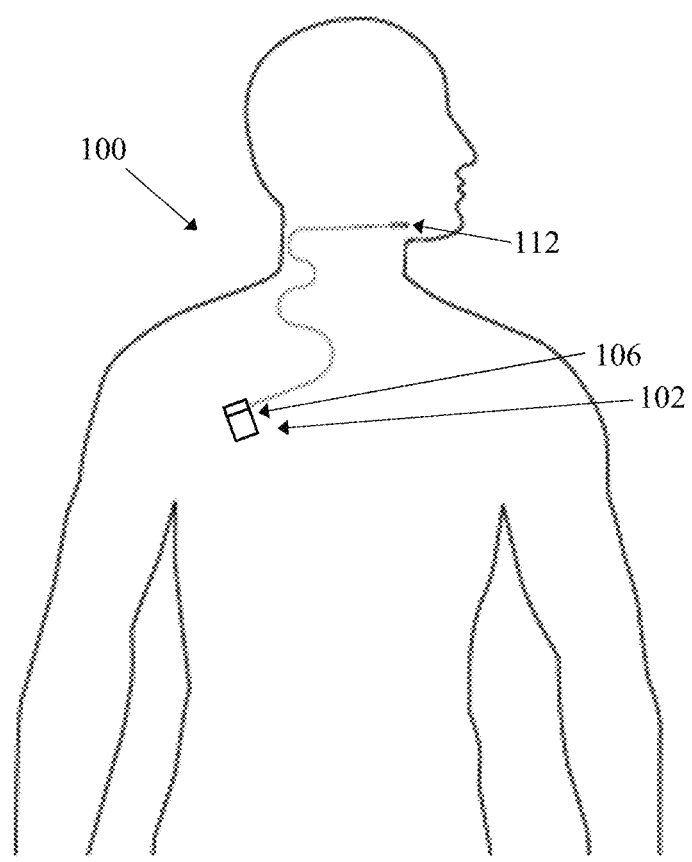
FIG. 1 is a diagram illustrating an exemplary embodiment of a system for treating obstructive sleep apnea using an implantable pulse generator, a cuff electrode on the Hypoglossal nerve and an inertial measurement unit to detect breathing activity.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Several aspects of exemplary embodiments according to the present disclosure will now be presented with reference to various systems and methods. These systems and methods will be described in the following detailed description and illustrated in the accompanying drawings by various blocks, components, circuits, processes, algorithms, etc. (collectively referred to as "elements"). These elements may be implemented using electronic hardware, computer software, or any combination thereof. Whether such elements are implemented as hardware or software depends upon the particular application and design constraints imposed on the overall system.

By way of example, an element, or any portion of an element, or any combination of elements may be implemented as a "processing system" that includes one or more processors. Examples of processors include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), application-specific integrated circuits (ASICs), state machines, gated logic, discrete hardware circuits, and other suitable hardware configured to perform the various functionality described throughout this disclosure. One or more processors in the processing system may execute software. Software shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise.

Accordingly, in one or more exemplary embodiments, the functions described may be implemented in hardware, software, or any combination thereof. If implemented in software, the functions may be stored on or encoded as one or more instructions or code on a computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by a computer.

FIG. 1 is a diagram illustrating an embodiment of a system 100 for treating obstructive sleep apnea using an IMU 102. It is envisioned that the IMU 102 may comprise an accelerometer and/or a gyroscope, and be configured to detect movement by a patient during the inspiration and expiration stages of a respiratory cycle (e.g., movement of the thoracic or abdominal cavity of the patient). In some aspects, the accelerometer and/or the gyroscope component may be capable of detecting motion and/or orientation along three axes. The IMU 102 may be configured to generate positional data based on the detected movement. Positional data may comprise, e.g., data indicative of the degree or speed of motion of the patient's chest (or one or more portions thereof), and/or orientation data for the patient. In some aspects, absolute or relative timing parameters for any detected motion is derived from positional data. In some aspects, an AC component of the IMU 102 data provides chest and/or abdominal movement data and the DC components provide subject orientation data.

In this example, the IMU 102 positioned within the housing containing the stimulation system 106 (e.g., an IPG). The inclusion of an IMU within the housing of an IPG may be advantageous in that it reduces the need for an additional surgical procedure to implant the IMU 102. Indeed, as noted above, prior systems which utilize a pressure sensor to detect motion to detect movement of the patient's thoracic or abdominal cavity during respiration typically require implantation of a sensor in-between a patient's ribs. This requires significant surgical time and tunneling a lead to this space is invasive, resulting in a longer recovery time. Accordingly, the present IMU-based systems are advantageous in that they are able to provide similar respiratory without the need for prolonged surgical and recovery time (i.e., in view of the fact that the IMU 102 can be integrated into the IPG's housing or implanted in proximity thereto in a separate housing).

Figure 2:
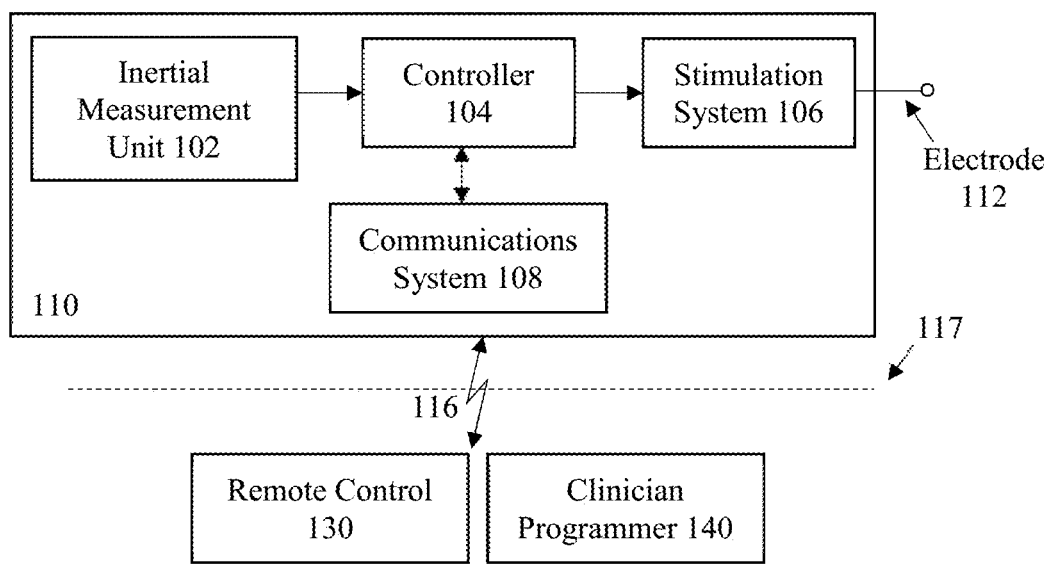
FIG. 2 is a block diagram illustrating an exemplary embodiment of a system for treating obstructive sleep apnea.

FIG. 2 is a block diagram of an exemplary embodiment of a system 100 for treating obstructive sleep apnea. It includes an implantable stimulator 110, an optional remote control 130, and a clinician programmer 140. In this example, the stimulator 110 includes an IMU 102, a controller 104, a stimulation system 106 (e.g., an IPG), an electrode 112 which may be used to stimulate a respiratory system muscle, and a communications system 108.

The IMU 102 may be configured to detect and/or measure movement (e.g., chest and/or abdominal movement) and orientation of a patient, and this positional data can be processed in turn by the controller 104 to determine the respiratory cycle of the patient. The stimulation system 106 (e.g., an implantable pulse generator, "IPG") may be configured to apply stimulation to the electrode 112. The controller 104 may be configured to control when and/or how the stimulation system 106 applies stimulation to the electrode 112. The controller 104 may be configured to determine the respiratory waveform of a patient (e.g., a human subject), or a model of the respiratory waveform based at least in part on the positional data from the IMU 102, and to control the stimulation system 106 based on the respiratory waveform or model respiratory waveform. For example, the controller 104 may trigger the stimulation system 106 to apply stimulation during the inspiratory period of the respiration waveform, to apply stimulation during the expiratory period of the respiratory waveform, or to apply stimulation during particular parts of the inspiratory and/or expiratory portions of the respiratory waveform (e.g., stimulation may be applied throughout inspiration and expiration, for every other respiratory cycle of the patient).

The communications system 108 may provide one or more wireless links 116, through the skin 117 of a patient, to the remote control 130, and/or a clinician programmer 140. The remote control 130, and the clinician programmer 140 may also include respective communications systems, which may provide wireless links 116 between the remote control 130, the clinician programmer 140, and/or additional Internet or cloud-based services. Any or all of these wireless links 116 can utilize Bluetooth, Bluetooth Low Energy, or other wireless communication protocols. The wireless links 116 may include authentication and encryption suitable to protect patient data.

In some embodiments, systems according to the disclosure may optionally include additional sensors, such as an acoustic sensor 109 (e.g., a microphone) and/or an ECG sensor 111. These optional additional sensors may be configured to determine whether or a degree to which the patient is breathing ("respiratory effect" data). Such data may be used in conjunction with positional data based on signals from the accelerometer and/or gyroscope component of the IMU 102, which provide information about movement of the patient's chest and/or abdomen ("respiratory effort" data). If the chest moves and there is no associated sound, the patient may be presumed to be experiencing an obstructive apnea. If a respiratory period (e.g. 10 seconds) passes and there is neither respiratory effort nor respiratory effect, then the patient may be presumed to be experiencing a central apnea. In some aspects, one or more of the aforementioned sensors can be used to detect increased effort and/or reduced air flow (e.g., by comparison to a predetermined threshold or historical respiratory cycle data). This equates to a hypopnea. In some aspects, embodiments of the present systems may leverage this ability to detect both increased effort and reduced air flow with an implant to determine an apnea-hypopnea index (AHI) for the patient, which is an indicator of the severity of OSA.

In some aspects, the AHI (or other sleep quality metric) may be used to automatically determine OSA severity and/or effectiveness of a treatment (e.g., a specific device, regimen, parameters). For example, OSA stimulator implants are typically not used during the first month after implantation. This allows for fixation of the cuff electrode around the hypoglossal nerve. Systems according to the disclosure may utilize sensory data collected from the UMI (and optionally also from an acoustic sensor 109 or ECG 11) to measure AHI for each night of sleep during the patient's recovery period. The AHI may in turn be used to determine a baseline or average AHI before therapy begins. This controller 104 may be configured to use this baseline for determining the effectiveness of the therapy after the system is activated following the recovery period. In addition, either the controller 104 or the clinician programmer 140 may be able to detect system faults by monitoring the nightly AHI to see if it returns to the baseline level determined based on data collected during the post-operative recovery period. In addition, if the AHI increases, it may indicate a broken lead, a dislodged cuff electrode, or another problem with the stimulation system 106.

The system 100 may be configured to deliver stimulation to a nerve innervating the upper airway of the patient through the electrode 112 implanted proximate to the nerve. In some embodiments, the nerve is the hypoglossal nerve. In some embodiments, the upper airway muscle comprises the genioglossus, the geniohyoid, or some combination thereof. When the nerve is stimulated, it activates the upper airway muscle, thereby preventing or alleviating obstructive apneic events. In some embodiments, the stimulation system 106 applies stimulation to the nerve with an intensity sufficient to promote tonus in the upper airway muscle. In some embodiments, the stimulation system 106 applies stimulation to the nerve with an intensity sufficient to cause bulk muscle movement in the upper airway muscle. The stimulation system 106 is coupled to controller 104. The controller 104 receives the sensory data from one or more internal sensors 109 and/or from the IMU 102, and controls when the stimulation system 106 applies stimulation. In some embodiments, the controller 104 can control the intensity of the stimulation applied by the stimulation system 106. In some embodiments, the stimulation system 106 may apply different intensities of stimulation by changing the amplitude, the pulse width, or the frequency of the stimulation. In some aspects, the control 104 controls the amplitude, the pulse width, or the frequency of the stimulation applied by the stimulation system 106.

The stimulator 110 may be configured to receive sensory data from an IMU 102 (e.g., positioned within a housing containing the IPG) and to apply stimulation therapy to the patient based on the sensory data received from the IMU 102. Apneic events can be detected by determining that the regular respiratory pattern has become irregular for a number of cycles (e.g., at least 1, 2, 3, 4, 5, 6, 7, 8, 9, or 10 cycles). Waveforms and parameters indicative of an irregular respiratory pattern are disclosed, e.g., in U.S. Pat. Nos. 5,540,731 and 8,938,299, the entire contents of which are incorporated herein by reference. Positional data obtained from the IMU 102 may be used by the controller 104 for apnea detection (e.g., heart rate rhythm and variability), providing potential benefits such as increased accuracy with respect to the administration of stimulation as a treatment for OSA.

In some aspects, the system 100 may use the positional data generated by the IMU 102 to dynamically titrate therapy delivered to the patient, to determine when to apply stimulation to the patient, and/or when to turn stimulation therapy on or off. For example, the controller 104 may provide orientation information obtained by processing one or more signals from the accelerometer and/or gyroscope components of the IMU 102, to make sleep orientation decisions. In some embodiments, the controller 104 may use machine learning methods to make the sleep stage decisions. The controller 104 may control the stimulation applied by the stimulation system 106 based on the sleep stage decisions. For example, the controller 104 may utilize the sleep stage decisions to determine whether to turn stimulation therapy on and off (e.g., turning stimulation therapy on when the sleep stage decisions indicate that the patient is asleep, turning stimulation therapy off when the sleep stage decisions indicate that the patient is not asleep).

In some aspects, the system 100 may use the positional data generated by the IMU 102 to determine parameters of the application of stimulation applied to the patient (e.g., where stimulation is applied during specific parts of the respiratory cycle, when to apply stimulation, and/or intensity of stimulation applied). For example, signals obtained from the accelerometer and/or gyroscope components of the IMU 102 may be processed to determine the respiratory cycle of the patient. The controller 104 may utilize this positional data, optionally in combination with sensory data from an acoustic sensor 109 or ECG 111, to evaluate or measure the respiratory cycle and control when stimulation is applied to the nerve during the respiratory cycle.

In some aspects, the system 100 may use the positional data generated by the IMU 102 to control when to turn therapy on or off. For example, in some embodiments, positional data generated by the IMU 102 to determine sleep stage, in addition to signals useful for detecting apneic events. Such systems can therefore also be used to turn on therapy at night and/or to dynamically titrate therapy based on the AHI, which as noted above is an indication of the severity of a person's sleep apnea.

The remote control 130 may communicate with the stimulator 110 to control aspects of the operation of the stimulator 110 based on user input received at the remote control 130. For example, the remote control 130 may be configured to receive a user input identifying a selected intensity for treatment. The remote control 130 may communicate the selected intensity to the stimulator 110 via the communications system 108, and the controller 104 may control the intensity of therapy applied based on the selected intensity. In another example, the remote control 130 may be configured to receive a user input selecting an on/off state for the system 100. The remote control 130 may communicate the selected on/off state to the stimulator 110 via the communications system 108, and the controller 104 may control whether therapy is applied by the stimulator 110 based on the selected on-off state. The clinician programmer 140 may be configured to receive user input (e.g., from a clinician configuring the stimulator 110) and to transmit the user input to the stimulator 110 via the communications system 108. The user input received from the clinician programmer 140 may be configuration information for operation of the stimulator 110 (e.g., identifying contacts of a multi-contact electrode to which stimulation should be applied; identifying an intensity of stimulation to be applied or a range of allowed intensities), and the controller 104, the stimulation system 106, or another element of the simulator 110 may operate based on the received configuration information. The remote control 130 and/or the clinician programmer 140 may be implemented using a smartphone, tablet, or other computing device configured with an application for communicating with the stimulator 110.

In some embodiments, the Internet and/or cloud services 150 may provide a history related to OSA treatment for the patient. For example, the stimulator 110 may transmit data related to therapy applied (e.g., duration of applied stimulation or intensity of applied stimulation) or related to efficacy of treatment (e.g., AHI) to the remote control 130 or to the clinician programmer 140, and the remote control 130 or the clinician programmer 140 may transmit the data to the Internet and/or cloud service 150 to be compiled. In some embodiments, the Internet and/or cloud services 150 may provide for remote monitoring of OSA treatment for the patient. For example, the data related to therapy applied or related to efficacy of treatment may be compiled and made accessible to a doctor or clinician providing OSA treatment for the patient. In some aspects, the stimulator 110 may transmit the data related to therapy applied or related to efficacy of treatment to the remote control 130, the remote control 130 may transmit the data to the Internet and/or cloud services 150, and the clinician programmer 140 may access and display the compiled data to assist the user of the clinician programmer 140 in the configuration of the stimulator 110. In some embodiments, the Internet and/or cloud services 150 may provide for remote updating of OSA treatment for the patient. For example, the clinician or doctor may make configuration changes via the Internet and/or cloud services 150, and the Internet and/or cloud services 150 may transmit the configuration changes to the stimulator 110 via the remote control 130 or the clinician programmer 140.

As described in further detail herein, the positional data generated by the IMU 102 (or optionally provided by an acoustic sensor 109 or ECG 111) may need to be subject to signal processing via one or more analog or digital filters (e.g., one or more low or HPFs, arranged in series or in parallel) in order to generate useful information. For example, the IMU 102 may pick up extraneous movement signals (e.g., heartbeat and snoring sounds), that may need to be filtered out to selectively identify the soft and low-pitched sounds arising from inspiration and expiration. In some aspects, digital filters will be preferable. However, implementations that perform analog filtering may be simpler and will often be more energy efficient.

In some aspects, positional data from one of the IMU sensors (e.g. from the accelerometer) may be filtered with a BPF. The low pass filter may be designed to pass respiration frequencies, while blocking cardiac frequencies and other sources of noise. For example, an upper cut-off frequency of 0.45 to 2 Hz would typically suffice to separate noise from the respiration signal. In some aspects, this filter could be an adaptive filter. A HPF may optionally be applied to eliminate any DC offset, with a high pass cut-off frequency of 0.05 to 0.1 Hz typically being sufficient in this regard.

Figure 3:
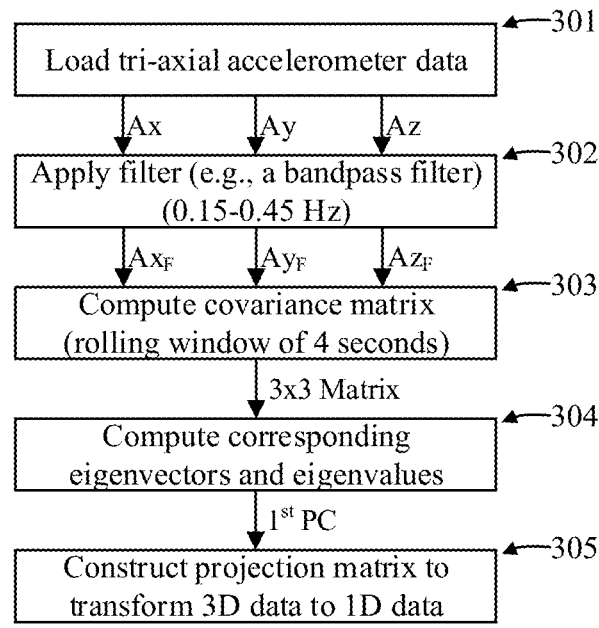
FIG. 3 is a flowchart illustrating aspects of a respiration detection algorithm based on a principal component analysis (PCA) that may be implemented by any of the systems described herein. The flowchart consists of a low pass filter to suppress high frequency noise and PCA for dimensionality reduction.
Figure 4:
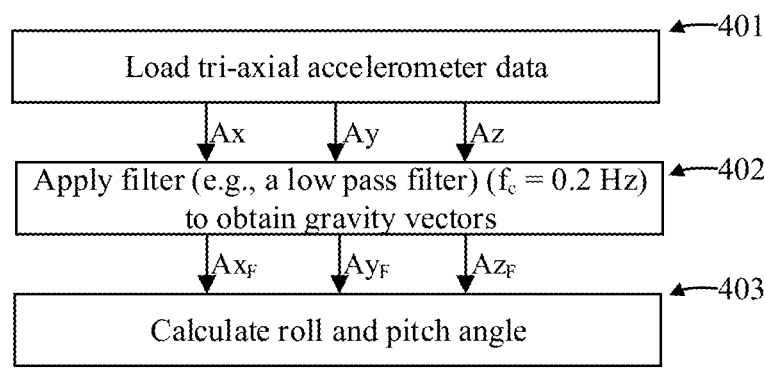
FIG. 4 is a flowchart illustrating computation of pitch and roll angle to find subject orientation.
Figure 5:
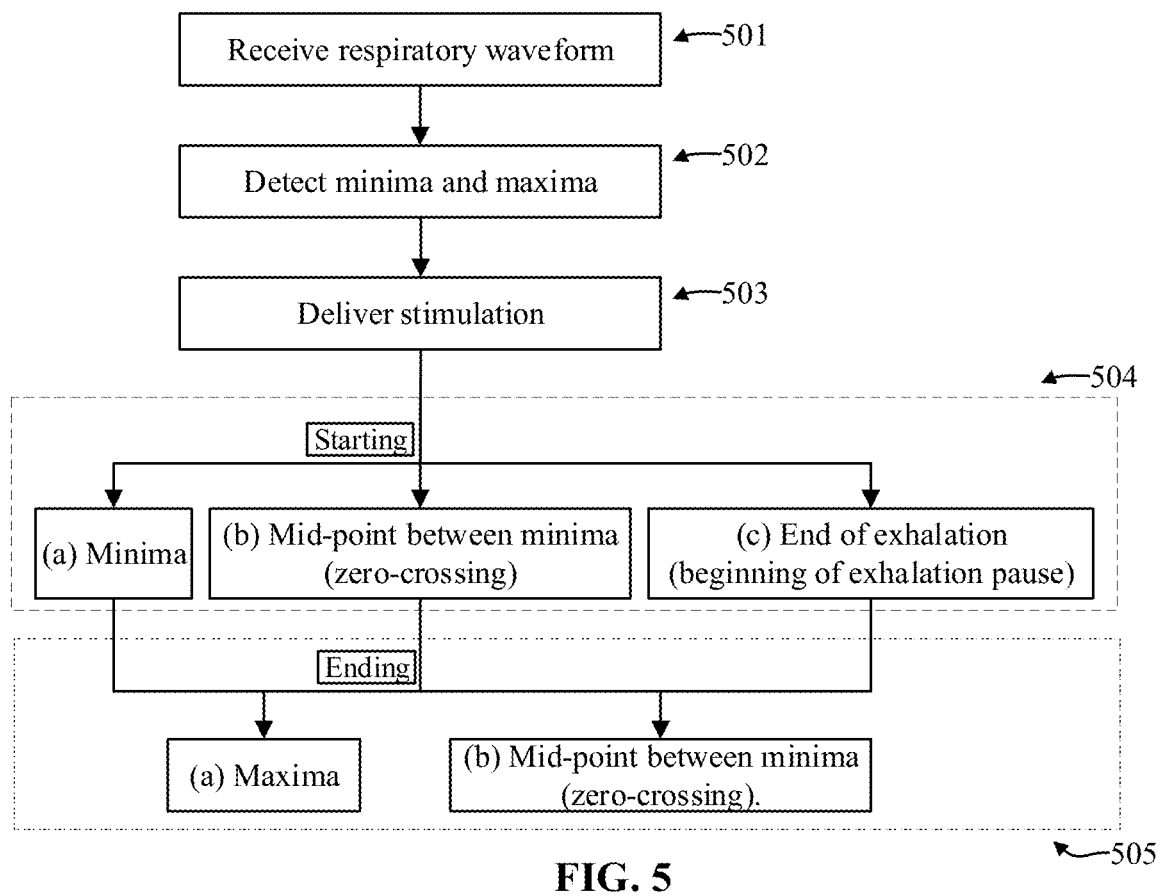
FIG. 5 is a flowchart illustrating aspects of minima and maxima detection of the respiratory waveform to deliver stimulation pulses synchronously to inspiration.

FIGS. 3-5 illustrate an exemplary method for determining the respiratory cycle of a patient by performing a PCA on filtered positional data generated by the IMU 102. For convenience, this method is separated into three stages. FIG. 3 describes an exemplary method for obtaining a breathing vector, whereas FIG. 4 describes a method for determining the orientation of the patient. Finally, FIG. 5 describes a method for determining when to apply stimulation.

As shown by FIG. 3, the signal from a tri-axial accelerometer component of the IMU 102 may be subjected to a PCA to reduce the dimensionality of the positional data. The process may begin by loading the signal (301) and processing it (302) using a bandpass filter (0.15 to 0.45 Hz). The processing may be performed by an analog filter or a digital implementation (e.g., by the controller 104). A covariance matrix may then be computed (303), e.g., using a rolling or stepped window of at least 4 seconds. Next, corresponding eigenvectors and eigenvalues may be computed for the matrix (304) and a projection matrix may be constructed to transform the 3D positional data into a single dimension (305), providing a respiration vector for the patient.

The signal processing steps illustrated by FIG. 3 may be performed or controlled by the controller 104. In some aspects, this signal processing may be performed in hardware, in software, or a combination thereof. Moreover, it is understood that the parameters shown in FIG. 3 are exemplary (e.g., at step 303 a rolling or stepped window of 2, 3, 4, 5, 6, 7, 8, 9, 10, or any other desired range may be used as desired for a given implementation).

FIG. 4 illustrates an exemplary method for determining the orientation (roll and pitch angle) of the patient. Orientation may be used to determine whether the patient is in a vertical (awake) or horizontal (sleep) position. Furthermore, the roll angle determines patient's sleep orientation (left or right lateral recumbent, prone, supine, or somewhere in between). Initial calibration of the sensor frame with respect to patient orientation after implantation can be used to accurately detect patient orientation using a tri-axial accelerometer (e.g., integrated into the IMU 102). This method may begin by loading (401) positional data obtained from the tri-axial accelerometer. Next, the signal may be filtered (402) using a HPF with center frequency at 0.05 to 0.1 Hz to obtain gravity vectors. Finally, the roll and pitch angle of the patient may be determined using these gravity vectors (403). In this implementation, HPF removes everything but the DC (or near-DC) components of the signal. In alternative aspects, a weighted finite impulse response (FIR) or infinite impulse response (IIR) LPF filter may suffice. In some aspects, sleep orientation may be used as a trigger to compute a new principal component for an updated orientation (e.g., instead of a fixed time window).

FIG. 5 illustrates the use of a respiratory cycle waveform generated from the 1D positional data resulting from a PCA of IMU 102 chest positional data (e.g., as exemplified by the method shown in FIG. 3). The controller 104 may evaluate the respiratory cycle waveform in order to detect minima and maxima (502) and to deliver stimulation (503) using the stimulator 110. The starting point and end point for stimulation may vary in different implementations. As illustrated by FIG. 5, stimulation may start at an (a) local minimum point in the respiratory cycle, (b) at a mid-point between a local minimum and maximum point (a "zero-crossing" event) or (c) at the end of exhalation (e.g., at the beginning of the exhalation pause). Stimulation may end at an (a) local maximum point in the respiratory cycle or (b) at a mid-point between a local minimum and maximum point (a "zero-crossing" event). It is understood that in some aspects, the starting point and stopping point for stimulation applied by the systems described herein may comprise a combination of the foregoing respiratory cycle events. Alternative starting and end point configurations may be desirable in certain embodiments. For example, if a detected respiratory cycle waveform minimum does not occur early enough before the start of inspiration, the controller 104 may be configured to shift the start and/or end of stimulation to other respiratory cycle waveform features, e.g., either of the zero-crossing events noted above. The zero-crossing events are close to, but not equivalent to the point where the respiratory cycle waveform slope starts to increase and to where it starts to decrease (i.e., local minima and maxima of the respiratory cycle waveform derivative).

It is understood that the methods illustrated by FIGS. 3-5 are exemplary in nature and that the steps described herein may be combined to generate alternative embodiments. Moreover, it is understood that any of the stimulation schedules described herein may be utilized in combination with any of the methods used to generate a respiratory cycle waveform for a patient (e.g., the stimulation schedules described in FIG. 5 may be used in embodiments wherein the respiratory cycle waveform was generated using alternative methods disclosed herein). Furthermore, it is contemplated that additional stimulation schedules are possible and compatible with the present systems and methods. In some aspects, a controller 104 may be configured to stimulate and pause for a duration that is a ratio of (e.g. 1.0, 1.1, 1.2, 1.3, 1.4, or 1.5 times) the average measured respiratory cycle period of the patient over a fixed trailing window. In other aspects, a controller 104 may be configured to stimulate and pause for a duration that is some ratio of a number of standard deviations from the mean of the average measured respiratory cycle period of the patient over a fixed trailing window. In still further aspects, a controller 104 may be configured to stimulate and pause for a duration that has been predetermined for a patient (e.g., either during a polysomnography study, during a clinic visit, or determined by analyzing respiration data collected between the IPG implantation and turning on stimulation). In others, it may be configured to stimulate and pause for a duration that has been predetermined for a subset of patients previously studied.

Figure 6:
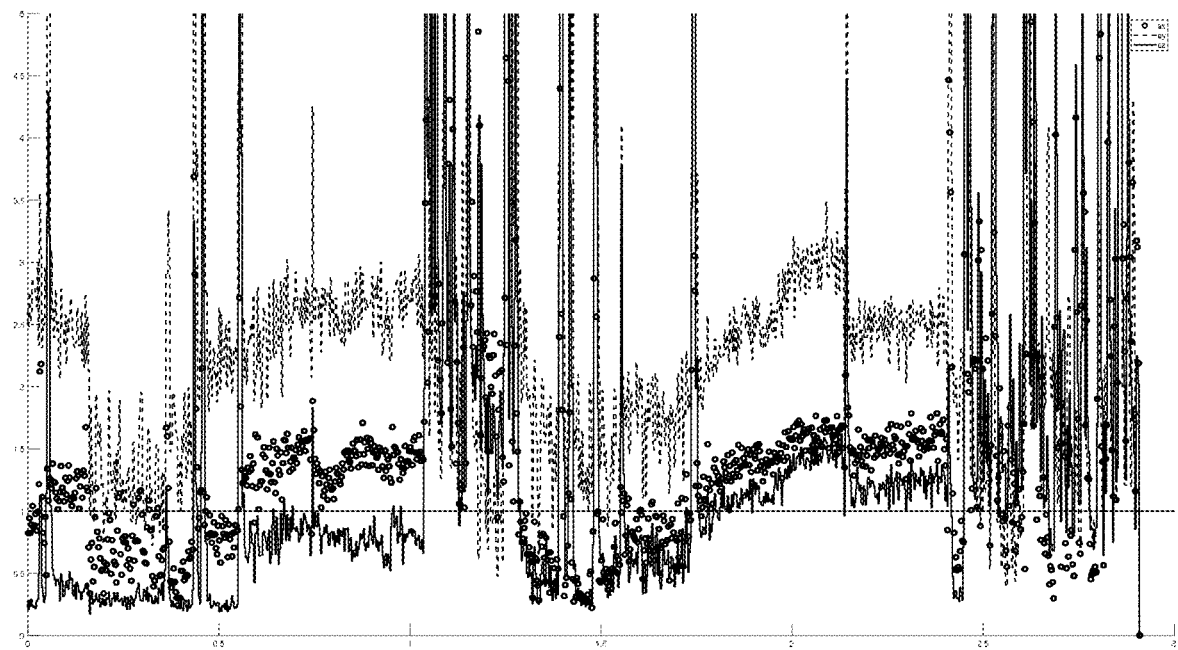
FIG. 6 is a graph illustrating a sample SNR computed from a 3-axis accelerometer component of an IMU (ax, ay, and az) used in the present systems. The horizontal line represents a pre-defined threshold. In some aspects of the present systems, the controller may be configured to switch to asynchronous mode if the SNR of at least two axes falls below a given threshold.
Figure 7:
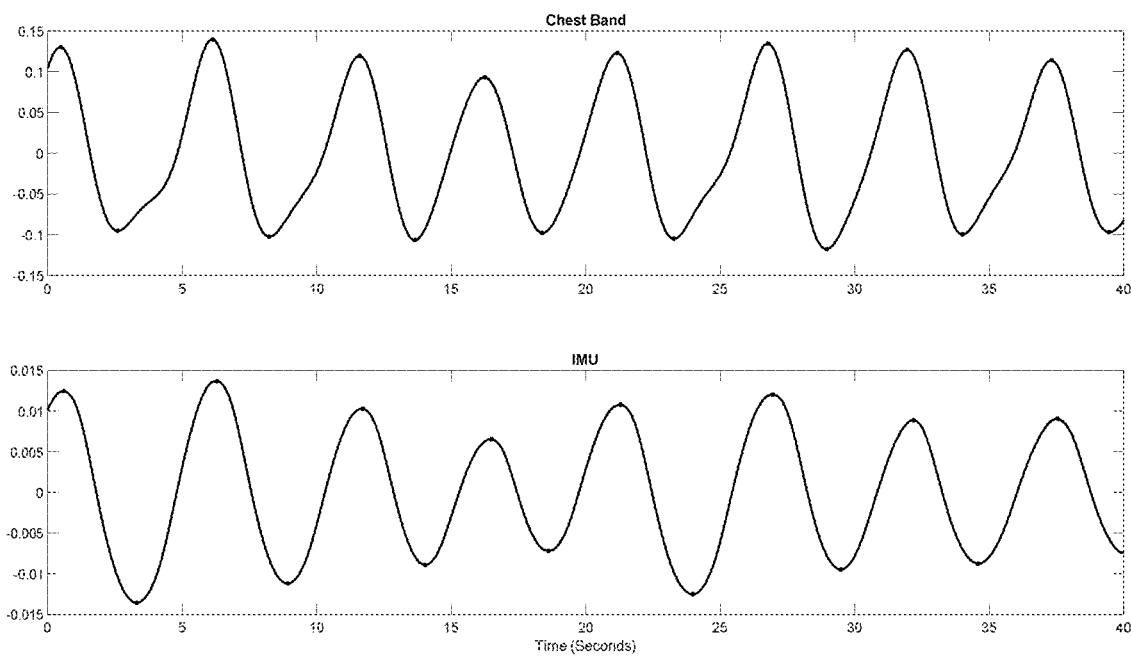
FIG. 7 includes a pair of graphs illustrating a respiratory cycle waveform with marked maximum and minimum from a control sensor, RIP band, (top plot) and from an IMU (bottom plot) for comparison. In some aspects, the controller may trigger an IPG to begin stimulation at a trough (start of inspiration) and to continue applying stimulation until the next peak (end of inspiration).

FIGS. 6-7 provide graphs which illustrate aspects of the signals and signal processing described herein.

FIG. 6 is a graph illustrating a sample SNR computed from a 3-axis accelerometer component of an IMU used in the present systems. The horizontal line represents a predefined threshold. In some aspects of the present systems, the controller may be configured to switch to asynchronous mode if the SNR of at least two axes of either the tri-axial accelerometer or the tri-axial gyro falls below a given threshold. A Teager-Kaiser Energy (TKE) operation or the envelop of the signal may be used to determine onset and duration of a motion artifact. The controller 104 may be configured to switch to asynchronous mode during a motion artifact, as discussed above. The large peaks are associated with motion artifact. They do not interfere with the calculations as they are above the threshold. Also motion artifact is already accounted for.

FIG. 7 includes a pair of graphs illustrating a respiratory cycle waveform with marked maximum and minimum from a control sensor (top plot) and from an IMU (bottom plot). In some aspects, the controller may trigger an IPG to begin stimulation at a trough (start of inspiration) and to continue applying stimulation until the next peak (end of inspiration). The peaks are troughs from the top and bottom plots are with +/−200 ms of each other.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

What is claimed is:

1. A system for treating obstructive sleep apnea, comprising:
    an inertial measurement unit (IMU) comprising an accelerometer and a gyroscope, wherein the IMU is configured to detect chest and/or abdominal movement by a patient during the inspiration and expiration stages of a respiratory cycle, and to generate chest and/or abdominal positional data based on the detected movement; and a stimulator comprising:
a stimulation system configured to deliver stimulation to a nerve which innervates an upper airway muscle; and
a controller coupled to the stimulation system, and to the IMU;
wherein the controller is
configured to determine a respiratory cycle of the patient by a) filtering the chest and/or abdominal positional data, and b) performing a principal component analysis (PCA) on the filtered chest and/or abdominal positional data, wherein the PCA comprises use of a covariance matrix generated using a rolling or stepped window of at least 4 seconds; and
configured to cause the stimulation system to stimulate the nerve based on the respiratory cycle of the patient.

2. The system of claim 1, wherein the accelerometer comprises a 3-axis accelerometer and/or the gyroscope comprises a 3-axis gyroscope.

3. The system of claim 1, wherein the positional data comprises movement of the chest and/or abdomen of the patient over time.

4. The system of claim 1, wherein the system further comprises a microphone and/or an electrocardiogram (ECG) sensor coupled to the controller.

5. The system of claim 1, wherein the controller is configured to determine an apnea-hypopnea index (AHI) based on (a) the positional data and (b) an audio signal detected by the microphone or a heart rate signal detected by the ECG sensor.

6. The system of claim 1, wherein the controller is further configured to cause the stimulation system to stimulate the nerve based on an audio signal detected by the microphone.

7. The system of claim 4, wherein the controller is further configured to cause the stimulation system to stimulate the nerve based on a heart rate signal detected by the ECG sensor.

8. The system of claim 1, wherein the system is configured to filter chest and/or abdominal positional data detected by the IMU using at least one low-pass filter (LPF), high-pass filter (HPF), or band-pass filter (BPF).

9. The system of claim 1, wherein the system is configured to filter chest and/or abdominal positional data detected by the IMU using a filter that has an upper cut-off frequency of 0.45 to 2 Hz.

10. The system of claim 1, wherein the system is configured to filter chest and/or abdominal positional data detected by the IMU using a filter that has a high-pass cut-off frequency of 0.05 to 0.1 Hz.

11. The system of claim 1, wherein the PCA comprises:
a) receiving a signal comprising 3D chest and/or abdominal positional data from the accelerometer component of the IMU, wherein the accelerometer comprises a 3-axis accelerometer and/or a 3D gyroscope;
b) processing the signal using at least one filter;
c) generating a covariance matrix based on the processed signal;
d) computing eigenvectors and eigenvalues for the covariance matrix; and
e) constructing a projection matrix that transforms the 3D chest and/or abdominal positional data into a single dimension.

12. The system of claim 1, wherein the controller is configured to determine a signal-to-noise ratio (SNR) of the positional data.

13. The system of claim 12, wherein the controller is configured to operate in an asynchronous mode when the SNR of the positional data falls below a predetermined threshold.

14. The system of claim 13, wherein the asynchronous mode comprises a mode wherein the controller is configured to cause the stimulation system to stimulate the nerve throughout a full respiration cycle, wherein the start of the respiratory cycle is predicted based on previously logged respiratory rate data.

15. The system of claim 13, wherein the asynchronous mode comprises a mode wherein the controller is configured to cause the stimulation system to stimulate the nerve:
a) for at least, exactly, or approximately 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 seconds;
b) for X-Y seconds, where "X" and "Y" are each independently selected from 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15;
c) for at least one full respiration cycle, wherein the start of the respiratory cycle is predicted based on previously logged respiratory rate data, and then optionally to cease stimulation for an equal amount of time; or
d) for at least one full respiration cycle, wherein the start of the respiratory cycle is predicted based on previously logged respiratory rate data, and then optionally to cease stimulation for at least, exactly, or approximately 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 seconds.

16. The system of claim 12, wherein the SNR is determined using historical positional data for the patient stored in a log.

17. The system of claim 12, wherein the SNR is determined based upon
a) at least two out of the three axes of the accelerometer; and/or
b) at least two out of the three axes of the gyroscope.

18. The system of claim 17, wherein the accelerometer is a 3-axis accelerometer and the controller is configured to determine whether the SNR of at least two out of the three axes of the accelerometer are above a predetermined threshold and to use the strongest component signal to determine the respiratory cycle of the patient.

19. The system of claim 17, wherein the gyroscope is a 3-axis gyroscope and the controller is configured to determine whether the SNR of at least two out of the three axes of the gyroscope are above a predetermined threshold and to use the strongest component signal to determine the respiratory cycle of the patient.

20. The system of claim 17, wherein the accelerometer is a 3-axis accelerometer and the controller is configured to determine a body orientation of the patient.

21. The system of claim 20, wherein the controller is configured to determine whether the patient is asleep based on the body orientation.

22. A method of treating obstructive sleep apnea in a patient comprising:
detecting chest and/or abdominal movement by the patient during the inspiration and expiration stages of a respiratory cycle using an inertial measurement unit (IMU) comprising an accelerometer and/or a gyroscope;

generating, by the IMU, chest and/or abdominal positional data based upon the detected movement, wherein the chest and/or abdominal positional data comprises information describing movement of the chest and/or abdomen of the patient, and optionally the patient's orientation;

determining, by a controller coupled to the IMU, a respiratory waveform corresponding to a respiratory cycle of the patient, using the chest and/or abdominal positional data; and stimulating a nerve innervating an upper airway muscle of the patient based on the respiratory waveform;

wherein the controller is configured to determine the respiratory waveform by: a) filtering the chest and/or abdominal positional data generated by the IMU, and b) performing a principal component analysis (PCA) on the filtered chest and/or abdominal positional data, wherein the PCA comprises use of a covariance matrix generated using a rolling or stepped window of at least 4 seconds.

23. The method of claim 22, wherein the PCA comprises:
a) receiving a signal comprising 3D chest and/or abdominal positional data from the accelerometer component of the IMU, wherein the accelerometer comprises a 3-axis accelerometer and/or a 3D gyroscope;
b) processing the signal using at least one filter;
c) generating a covariance matrix based on the processed signal;
d) computing eigenvectors and eigenvalues for the covariance matrix; and
e) constructing a projection matrix that transforms the 3D chest and/or abdominal positional data into a single dimension.

24. The method of claim 22, wherein the controller is configured to determine a signal-to-noise ratio (SNR) of the positional data, and to operate in an asynchronous mode when the SNR of the positional data falls below a predetermined threshold.

25. The method of claim 22, wherein the asynchronous mode comprises a mode wherein the controller is configured to cause the stimulation system to stimulate the nerve:
a) for at least, exactly, or approximately 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 seconds;
b) for X-Y seconds, where "X" and "Y" are each independently selected from 1, 1.5, 2, 2.5, 3, 3 5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15;
c) for at least one full respiration cycle, wherein the start of the respiratory cycle is predicted based on previously logged respiratory rate data, and then optionally to cease stimulation for an equal amount of time; or
d) for at least one full respiration cycle, wherein the start of the respiratory cycle is predicted based on previously logged respiratory rate data, and then optionally to cease stimulation for at least, exactly, or approximately 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 seconds.

26. A system for treating obstructive sleep apnea, comprising:
an inertial measurement unit (IMU) comprising an accelerometer and a gyroscope, wherein the IMU is configured to detect chest and/or abdominal movement by a patient during the inspiration and expiration stages of a respiratory cycle, and to generate chest and/or abdominal positional data based on the detected movement; and
a stimulator comprising:
a stimulation system configured to deliver stimulation to a nerve which innervates an upper airway muscle; and
a controller coupled to the stimulation system, and to the IMU;
wherein the controller is
configured to determine a respiratory cycle of the patient by performing a principal component analysis (PCA) using the chest and/or abdominal positional data generated by the IMU; and
configured to cause the stimulation system to stimulate the nerve based on the respiratory cycle of the patient;
wherein the controller is further configured to automatically switch to and operate in an asynchronous mode when the signal-to-noise ratio of the chest and/or abdominal positional data generated by the IMU falls below a predetermined threshold.

27. The system of claim 26, wherein the asynchronous mode comprises a mode wherein the controller is configured to cause the stimulation system to stimulate the nerve throughout a full respiration cycle, wherein the start of the respiratory cycle is predicted based on previously logged respiratory rate data for the patient.

* * * * *